United States Patent
Liu et al.

(10) Patent No.: US 9,265,423 B2
(45) Date of Patent: Feb. 23, 2016

(54) METALLIC OBJECT MR IMAGING QUALITY CONTROL SYSTEM

(71) Applicants: Kecheng Liu, Zhejiang Hangzhou (CN); Abraham Padua, Jr., Houston, TX (US)

(72) Inventors: Kecheng Liu, Zhejiang Hangzhou (CN); Abraham Padua, Jr., Houston, TX (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 192 days.

(21) Appl. No.: 13/763,775

(22) Filed: Feb. 11, 2013

(65) Prior Publication Data

US 2013/0301892 A1 Nov. 14, 2013

Related U.S. Application Data

(60) Provisional application No. 61/643,940, filed on May 8, 2012.

(51) Int. Cl.
*G06K 9/00* (2006.01)
*A61B 5/00* (2006.01)
*A61B 5/055* (2006.01)
*G01R 33/58* (2006.01)
*G01R 33/48* (2006.01)
*G01R 33/56* (2006.01)

(52) U.S. Cl.
CPC ........... *A61B 5/0033* (2013.01); *A61B 5/055* (2013.01); *A61B 5/7203* (2013.01); *G01R 33/58* (2013.01); *A61B 2560/0228* (2013.01); *G01R 33/4828* (2013.01); *G01R 33/5602* (2013.01); *G01R 33/5607* (2013.01)

(58) Field of Classification Search
None
See application file for complete search history.

(56) References Cited

U.S. PATENT DOCUMENTS

| | | | | |
|---|---|---|---|---|
| 5,590,655 | A * | 1/1997 | Hussman | 600/426 |
| 8,503,750 | B2 * | 8/2013 | Benson et al. | 382/131 |
| 2004/0107870 | A1 * | 6/2004 | Bae | C08K 3/22 |
| | | | | 106/286.5 |
| 2010/0098640 | A1 * | 4/2010 | Cohen | C07D 309/40 |
| | | | | 424/9.361 |
| 2010/0195885 | A1 * | 8/2010 | Ma | 382/131 |
| 2010/0254897 | A1 * | 10/2010 | Frank et al. | 424/1.29 |
| 2010/0329530 | A1 * | 12/2010 | Lang et al. | 382/131 |
| 2013/0138209 | A1 * | 5/2013 | Cragg et al. | 623/14.12 |

OTHER PUBLICATIONS

Datasheet, "NTC thermistors for temperature measurement, Probe assemblies", Series/Type: B57227 dated Mar. 2006, EPCOS AG 2006.
SYNGO MR ACR Quality Control Guidance v.2.0.PDF, Mar. 2006.
Matsuura H, Inoue T, Konno H, Sasaki M, Ogasawara K, Ogawa A. "Quantification of susceptibility artifacts produced on high-field magnetic resonance images by various biomaterials used for neurosurgical implants". Technical note. J Neurosurg. Dec. 2002;97(6):1472-5.

* cited by examiner

*Primary Examiner* — Nancy Bitar
(74) *Attorney, Agent, or Firm* — Peter R. Withstandley

(57) ABSTRACT

A system assesses quality of an image of human anatomical components in the presence of a metallic object. The system comprises an image processor for selecting an imaging protocol to use in imaging a test unit in response to data indicating a metal type employed in the test unit. The test unit includes, at least one object of the metal type used for a medical implant, an object comprising water and an object representing human fat. The water object and fat object are less than 3 centimeters, for example, distant from the metal object.

20 Claims, 11 Drawing Sheets

PRIOR ART

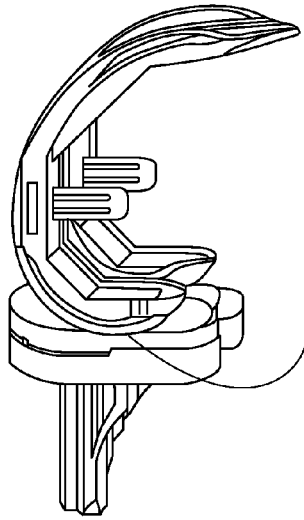

ANATOMIC RADIUS (10° - 110°)
- DESIGNED TO MAINTAIN COLLATERAL LIGAMENT STABILITY THROUGHOUT THE RANGE OF MOTION.
- CENTERED AT THE TRANSEPICONDYLAR AXIS THE OPTIMAL FLEXION AXIS OF THE KNEE.

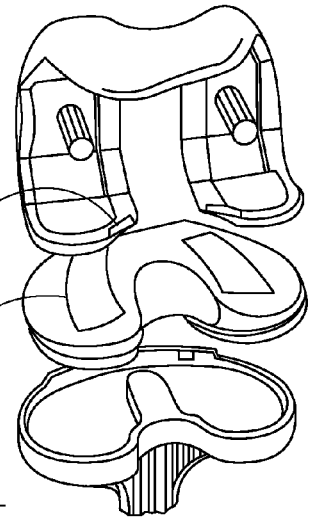

FLARED POSTERIOR CONDYLES
- OPEN DESIGN ACCOMMODATES 20 DEGREES OF INTERNAL/EXTERNAL ROTATION THROUGHOUT THE RANGE OF MOTION.

ROTARY ARC INSERT
- PRECISION-MACHINED SURFACE FACILITATES INTERNAL/EXTERNAL ROTATION

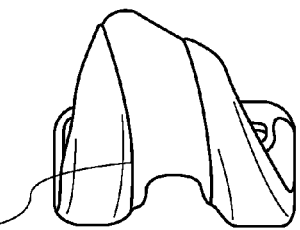

ANATOMIC PATELLOFEMORAL TRACK
THE TRIATHLON® KNEE PATELLOFEMORAL TRACK SHARES THE SAME DESIGN AS PRECEDING STRYKER® TOTAL KNEE SYSTEMS, BRINGING OVER A DECADE OF EXCELLENT CLINICAL PERFORMANCE AND THE INDUSTRY'S LOWEST REVISION RATE (0.3%) TO DATE IN THIS KNEE SYSTEM.

FIG. 1A

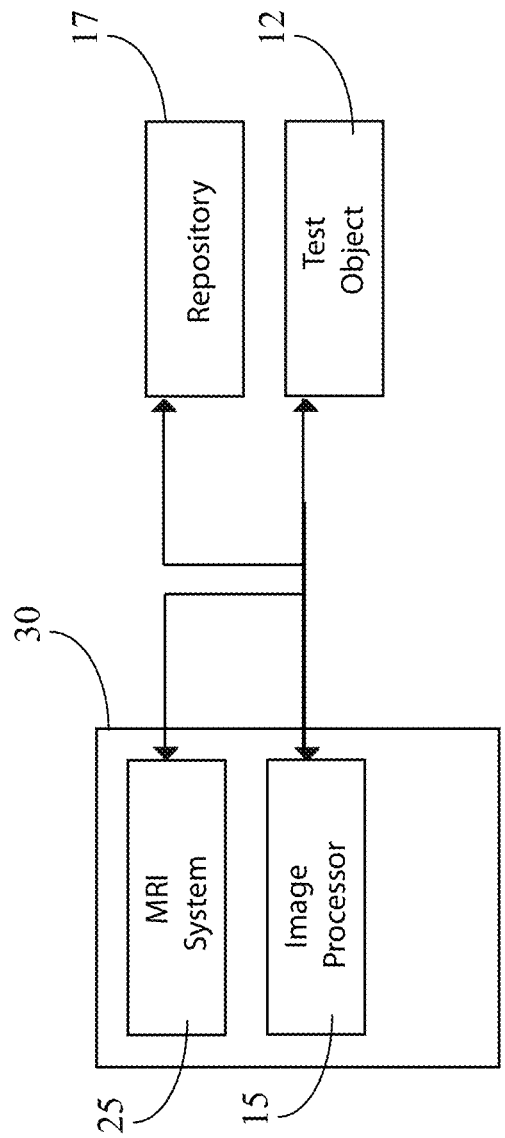

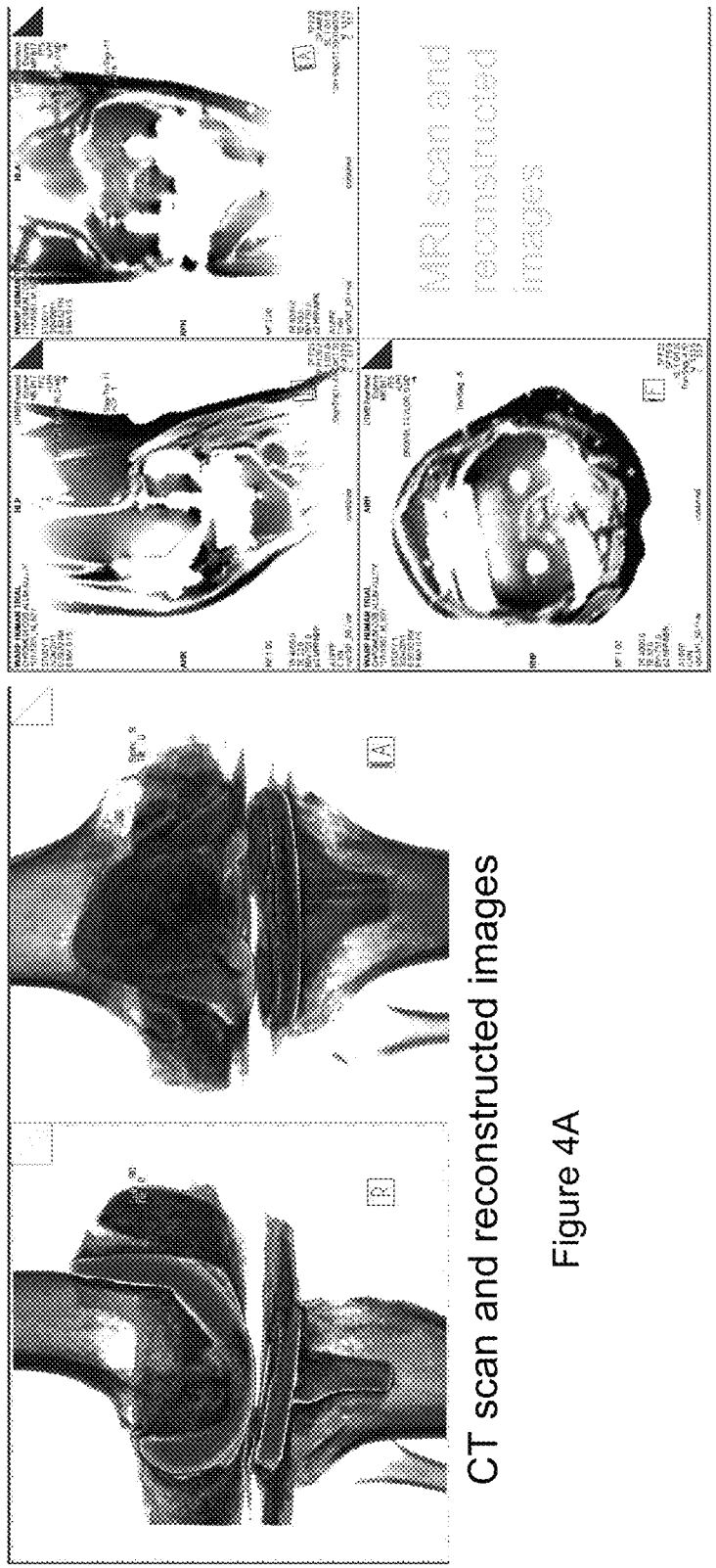
Figure 4A  CT scan and reconstructed images
Figure 4B  MRI scan and reconstructed images

METALLIC OBJECT MR IMAGING QUALITY CONTROL SYSTEM

This is a non-provisional application of provisional application Ser. No. 61/643,940 filed May 8, 2012, by K. Liu et al.

FIELD OF THE INVENTION

This invention concerns a test unit for imaging by an MR imaging system for use in assessing quality of an image of human anatomical components in the presence of a metallic object or another object with a substantial magnetic susceptibility effect by quantifying susceptibility artifacts and distortions.

BACKGROUND OF THE INVENTION

Magnetic Resonance imaging of joints that contain metal is a challenging task, due to a magnetic field susceptibility effect, which causes significant local field changes in the main static base MRI magnetic field (B0) and RF transmit coil field (B1). FIG. 1A shows a known metal joint used for a knee and FIG. 1B shows a known metal joint used for hip joint replacement, for example. Historically imaging metal joints was not a major problem partly because technically it was nearly impossible to perform MR scanning of metallic features, and partly because such scanning was not permitted due to its unknown effect and potential safety considerations. However, it is desirable to be able to perform post-surgical examination of joints with metal hardware. Known methods support metallic object imaging and assess metal object image quality qualitatively and subjectively. Such subjective assessment is dependent on human judgment and is vulnerable to associated error and provides inconsistent results. Known test objects (phantoms) used for assessing MRI image quality fail to support metal object imaging and are constructed of non-metallic materials and do not cause significant susceptibility effects. FIG. 2, for example, shows a known test object used for MR image quality checking and service tune-up comprising materials having no magnetic susceptibility effect. A test object and system according to invention principles addresses this need and associated problems.

SUMMARY OF THE INVENTION

A system according to invention principles provides a system and specific test objects (phantoms) usable for gauging quality of MR metallic object images by quantitative evaluation of image quality of the metal object images. A test unit is provided for imaging by an MR imaging system for use in assessing quality of an image of human anatomical components in the presence of a metallic object. The test object comprises, at least one object of a metal type used for a medical implant; an object comprising water and an object representing human fat. The water object and fat object are less than, for example, centimeters distant from the metal object. A system assesses quality of an image of human anatomical components in the presence of a metallic object. The system comprises an image processor for selecting an imaging protocol to use in imaging the test unit in response to data indicating a metal type employed in the test unit.

BRIEF DESCRIPTION OF THE DRAWING

FIG. 1A shows a known metal joint used for a knee and FIG. 1B shows a known metal joint used for hip joint replacement.

FIG. 3 shows a system for assessing quality of an image of human anatomical components in the presence of a metallic object, according to invention principles.

FIG. 4A shows two CT scan and reconstruction images and FIG. 4B shows corresponding MRI scan and reconstructed images.

DETAILED DESCRIPTION OF THE INVENTION

The inventors have advantageously recognized that a measure of fidelity of metal object images is desired for clinical diagnosis and this may be provided using a specific MRI test object (phantom) for image calibration. A test object is an inanimate object having known features that is imaged with the resultant image being usable to gauge fidelity of the imaging system in imaging an object having test object-like characteristics. The inventors have recognized that known test objects are unusable to quantitatively evaluate quality of MR images of metallic objects. A system according to invention principles provides specific test objects usable for gauging quality of MR metallic object images. CT (computer tomography) depicts artificial joints clearly but without soft tissue information (luminance contrast) where most pathological change occurs. MRI (Magnetic Resonance Imaging), in contrast, provides soft tissue information for clinical diagnosis. For patients requiring replacement of joints, like knee, hip or shoulder joints, for example, a radiologist needs to examine aspects in post-surgical examination including, whether a patient has an infection, whether a (metal) implant is loose, whether a patient has avascular necrosis (AVN) or osteolysis. This is facilitated with soft tissue image information.

Unfortunately, due to presence of metals, MRI images are degraded by distortion and signal voids, affecting clinical diagnosis. FIG. 4A shows two CT scan and reconstruction images and FIG. 4B shows corresponding MRI scan and reconstructed images. Specifically, the CT images of FIG. 4A clearly depict implanted metal hardware without showing soft tissues surrounding the implants. In contrast, the MRI images of FIG. 4B can show soft tissues but the details in the vicinity of metal implants are lost, significantly impairing clinical diagnostic value. In the presence of metal materials within an imaging area field of view (FOV), MRI difficulties include, a main static base MRI magnetic field (B0) locally changes due to magnetic susceptibility effect and an RF transmit coil field (B1) locally changes, because metal materials possess electro-magnetic properties absent from human tissue. In addition, the presence of metal materials within an imaging area (FOV), causes a potential heating effect, because of thermal conductive property of metal materials also absent from human tissues. The metal effects impair MRI images by causing signal voids and falsified hyper signal intensity due to distortion, i.e. mis-mapped morphology and distortion due to offset resonance also cause failure of some fat suppression methods to suppress fat signal. Further, contrast management for MRI images presents another difficulty. In the presence of inhomogeneous B0 and B1 fields, spectral fat suppression, for instance, may be unachievable. Thus valuable image information around metal parts in joints is lost.

Figure 1B:
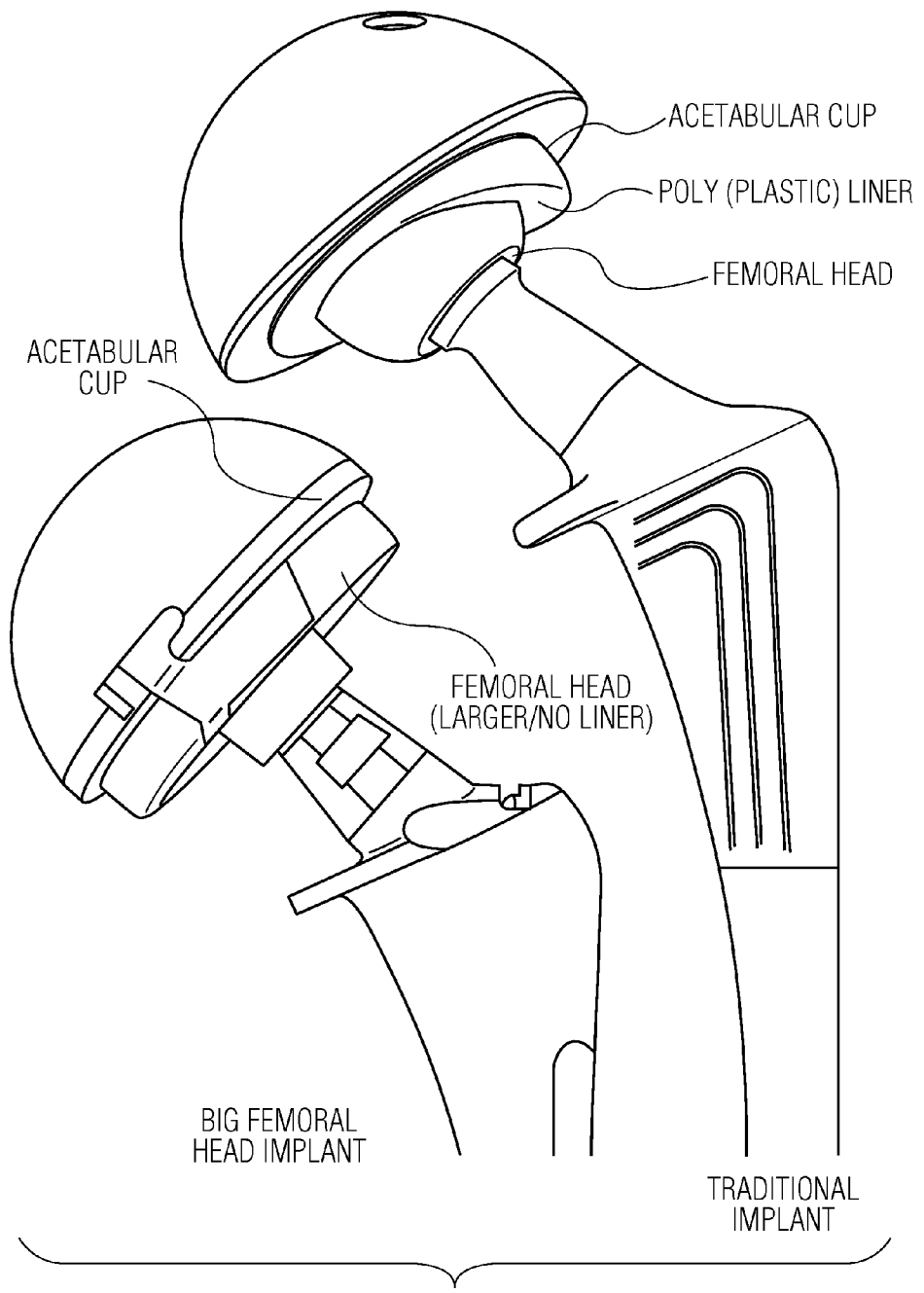
Figure 2:
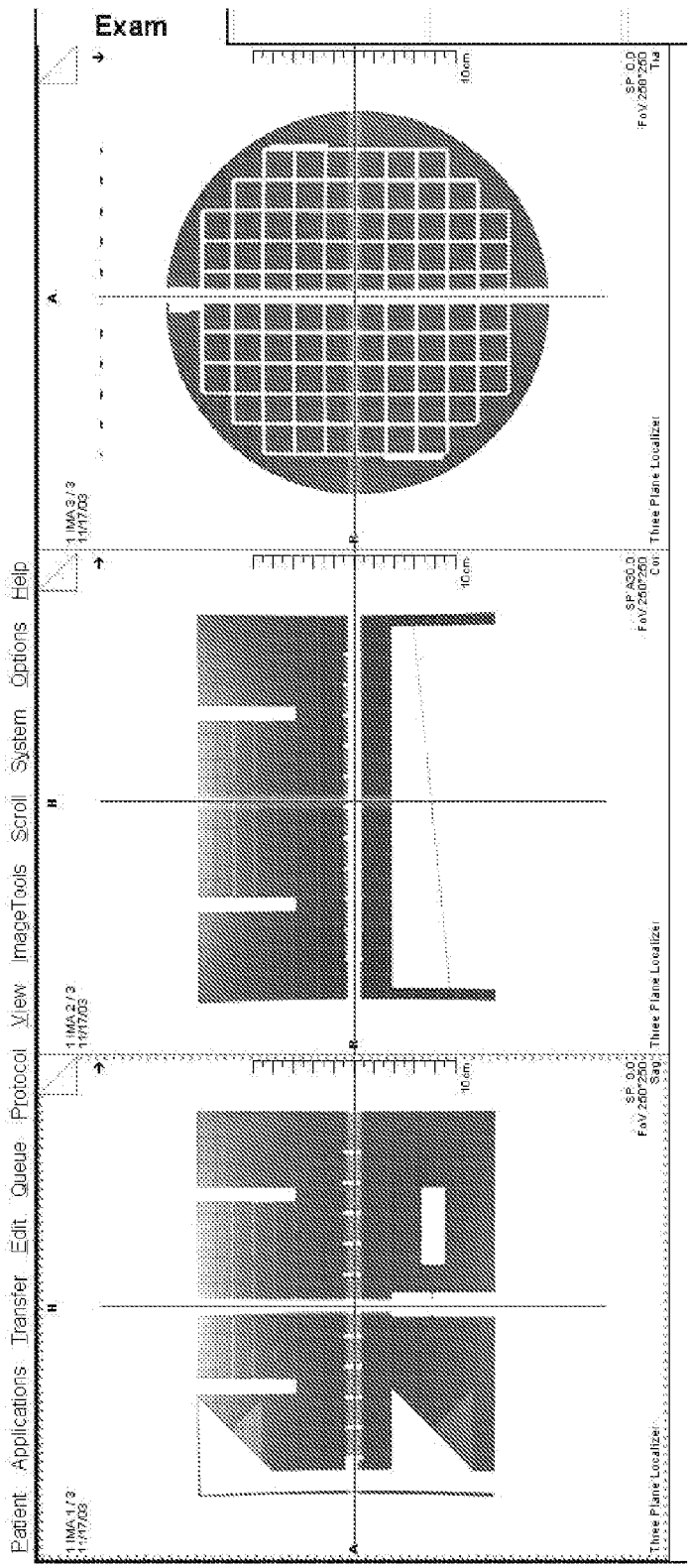
FIG. 2 shows a known test object used for MR imaging.
Figures 5A, 5B:
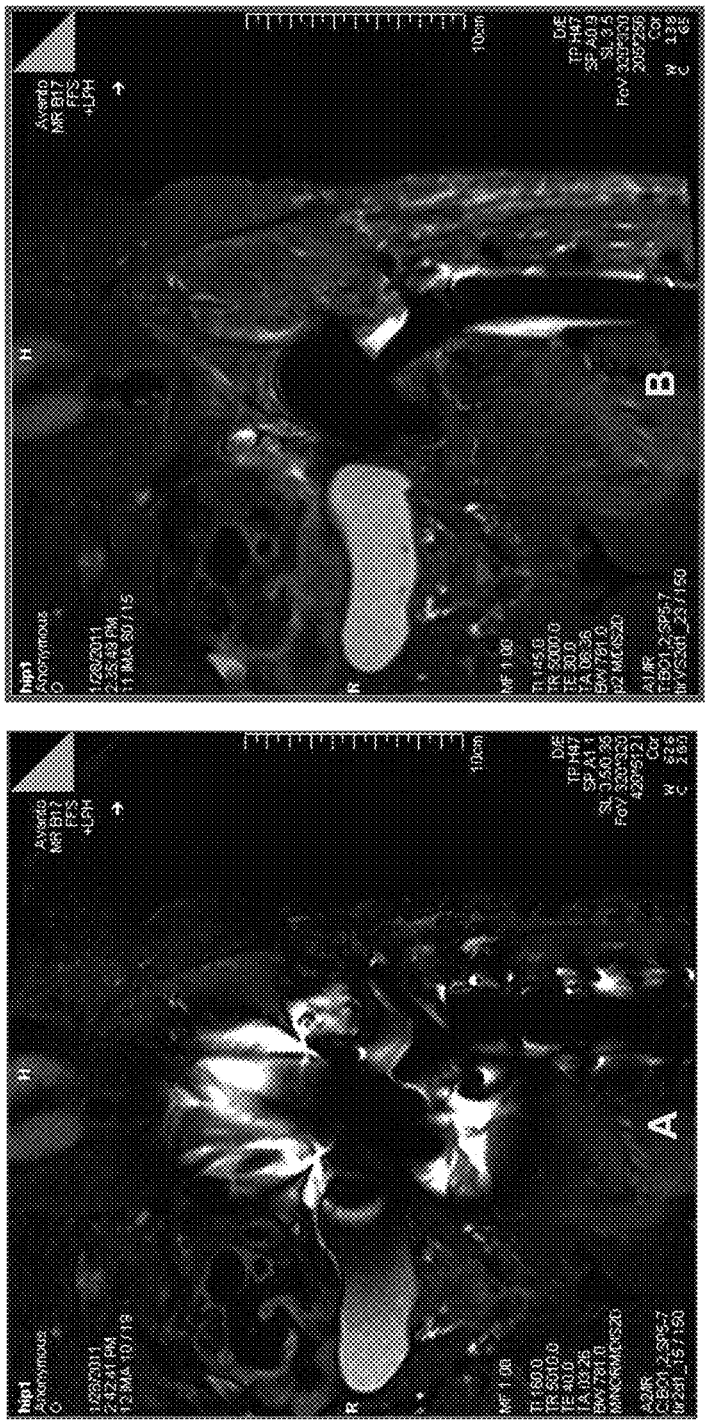
FIG. 5A shows an image acquired with a known imaging method and FIG. 5B shows an image acquired using a known metal imaging method with consideration of off-set frequency effects and dramatic reduction of artifacts.

FIG. 5A shows an image acquired with a known imaging method and FIG. 5B shows an image acquired using a known metal imaging method with consideration of offset frequency effects and dramatic reduction of artifacts. FIG. 5A shows an MR image illustrating unmitigated metal effects having image quality that is less than acceptable for clinical diagnosis, because of lost of information in the vicinity of metal parts. FIG. 5B shows improved images but the improvement remains relative and qualitative.

Image test objects are used for service purposes and are used to check B0 homogeneity, B1 homogeneity, spatial resolutions and slice profiles, for example. For metal imaging, although there are several methods to reduce metal object induced magnetic field susceptibility artifacts, there is a lack of a quantitative measure indicating fidelity of these methods and lack of a test object to provide a quantitative measure. Known systems rely on qualitative judgment of image quality subject to human error and inconsistency.

Figure 6:
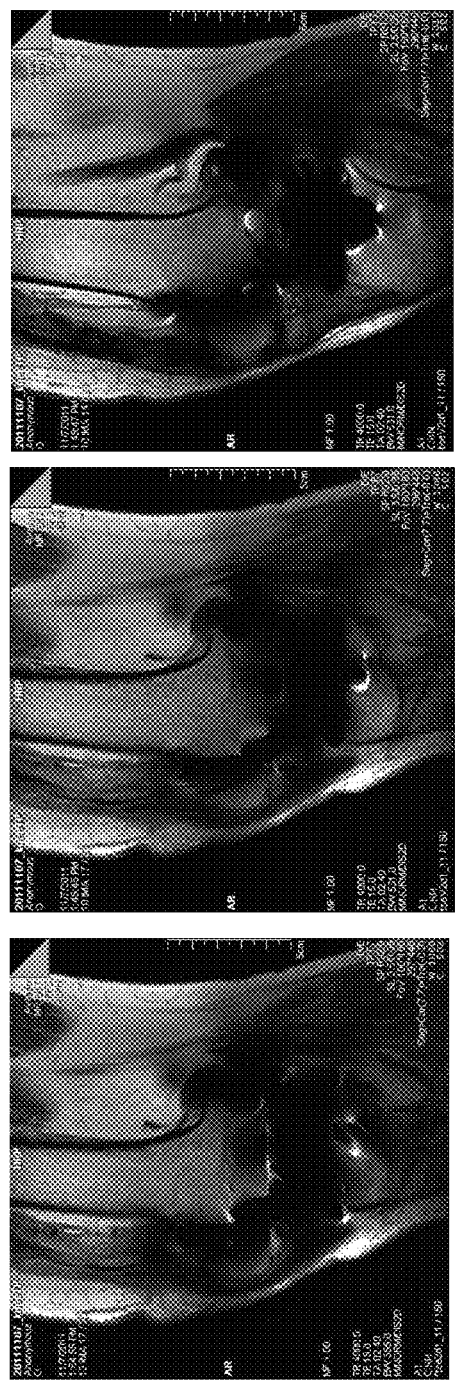
FIG. 6 shows metal implant images acquired with different known acquisition methods.

FIG. 6 shows three metal implant images acquired with different known acquisition methods illustrating the difficulty of providing MR images in the presence of metal objects that may be used for diagnostic purposes. The images fail to reveal the true shape of metal implants and the magnetic field susceptibility artifacts make it difficult to know the kind of luminance contrast range and range of other image information involved. Image interpretation is dependent on user reading experience and focus, which results in inconsistent interpretation, confusion, mis-understanding and potentially mis-diagnosis. The geometry (shapes) of real metal implants are irregular increasing difficulty in providing quantitative analysis.

FIG. 3 shows system 10 for assessing quality of an image of human anatomical components in the presence of a metallic object. System 10 includes, repository 17, test object 12 and imaging system 30 including an image processor 15 and MRI image acquisition device 25. Image processor 15 selects an imaging protocol to use for imaging test unit 12 in response to data indicating a metal type employed in test unit 12. Further, test unit 12 includes at least one object of the metal type used for a medical implant, an object comprising water and an object representing human fat. In one embodiment, the water object and fat object are less than 3 centimeters, for example, distant from the metal object. Image processor 15 uses information stored in repository 17 in selecting an imaging protocol to use in imaging test unit 12. The information associates multiple different imaging protocols with data identifying corresponding imaging and clinical procedures, metal types, anatomical regions to be imaged and imaging device characteristics.

In one embodiment, test unit 12 includes agar material and includes a temperature sensor attached to the metal object for measuring maximum temperature of the metal object during imaging. Alternatively, instead of Agar another material which can provide background signal can also be used. In an embodiment, unit 12 includes different metal objects of different metal types separated by a distance comprising at least 5 times a minimum diameter of the different metal objects. The different metal types include at least two of, (a) Titanium, (b) Stainless Steel, (c) Cobalt and (d) Chromium-Molybdenum Alloy. In another embodiment, the at least one object of the metal type comprises a real medical implant. Test unit 12 may also include an object of polyurethane plastic (manufactured to equal shape and size of metal pieces) used in medical implants as a reference against one or more metals to evaluate and quantify the extent of susceptibility and the extent of measurable or quantifiable improvements after imaging protocol optimization.

In an embodiment, a water object and a fat object are of known size and substantially adjacent the metal object, enabling determination of extent of degradation of image quality based on measurement of size of the water object or the fat object of known size in an image of the test unit. Specifically, the water object is of known size and substantially adjacent to, and the same size as, the metal object, enabling determination of extent of degradation of image quality based on measurement of size of the water object in an image of the test unit.

Image processor 15 uses the information in selecting at least one of, (a) an MR imaging bandwidth (BW) parameter and (b) a slice encoding, in response to data indicating the metal type employed in the test unit. In one embodiment, image processor 15 selects both an MR imaging bandwidth (BW) parameter and a slice encoding, substantially higher for cobalt than titanium. In another embodiment, image processor 15 selects the imaging protocol to use for fat suppression in imaging the test unit in response to data indicating a metal type employed in a test unit. The imaging protocol to use for fat suppression comprises at least one of, (a) a Spectral based fat suppression protocol using a pre-saturation pulse with fat resonance and water-excitation, (b) a STIR (Short Time Inversion Recovery) protocol and (c) a DIXON method imaging protocol.

The inventors have recognized that imaging quality in the presence of metal objects is quantitatively determinable using a dedicated susceptibility MRI test object. The test object advantageously includes, different materials which are commonly used for metal implants and comprising regularly shaped metal parts facilitating evaluation of susceptibility related artifacts. The test object also includes water and fat components (or fluids which mimic these components), in order to assess fat suppression imaging methods as well as imaged soft tissues. Temperature sensors (for instance R/T (resistance-temperature) type sensors), are coupled to the metal components to measure and evaluate temperature changes of the metal parts under different conditions, including MRI scanning with different sequences. In one embodiment, the test object has a sensor for measuring a SAR (Specific Absorption Rate) of RF energy of a component. The test object provides a spatial arrangement of metal parts in order to check image resolution in the vicinity of the metal parts. Commonly, metal materials in artificial joints are made of Titanium, Stainless Steel or Cobalt-Chromium-Molybdenum Alloy. Titanium presents relatively low magnetic field susceptibility in MRI images. Stainless Steel presents a medium level of magnetic field susceptibility in MRI images and Cobalt-Chromium-Molybdenum Alloy presents a relatively large magnetic field susceptibility effect in MRI images resulting in substantial MR image artifacts.

A test object with Titanium, Stainless Steel and Cobalt-Chromium-Molybdenum Alloy is advantageously used to evaluate different MRI methods, i.e. pulse sequences, for reduction of artifacts as well for imaging protocol optimization because the image quality in the presence of a magnetic field susceptibility effect depends on metal materials, magnetic field strength and field directions. In one embodiment, a test object contains multiple different types of metals with regular shapes, like rectangular bars or cylinders, multiple components of substances that mimic water and fat and temperature sensors which are connected to metal parts. Depending on electrical properties, at least one temperature sensor is connected onto the metal components which possess the greatest electric conductivity, to measure temperature changes in the case of substantial RF exposure. The water and fat components that mimic tissue are arranged to be in the proximity of metal components, to assess specific fat suppression methods in MRI with the distance between metal parts being sufficient to avoid interference between magnetic field susceptibility effects. The metal components are of different shapes (including a combination of one or more of, rectangular, cylinder, tube, ball shapes) and are accurately defined, for instance, for a rectangular bar of 10×10×50 mm. Thus by measuring a signal void area, artifacts can be quantified as being 20%, 30%, for example.

Figure 7:
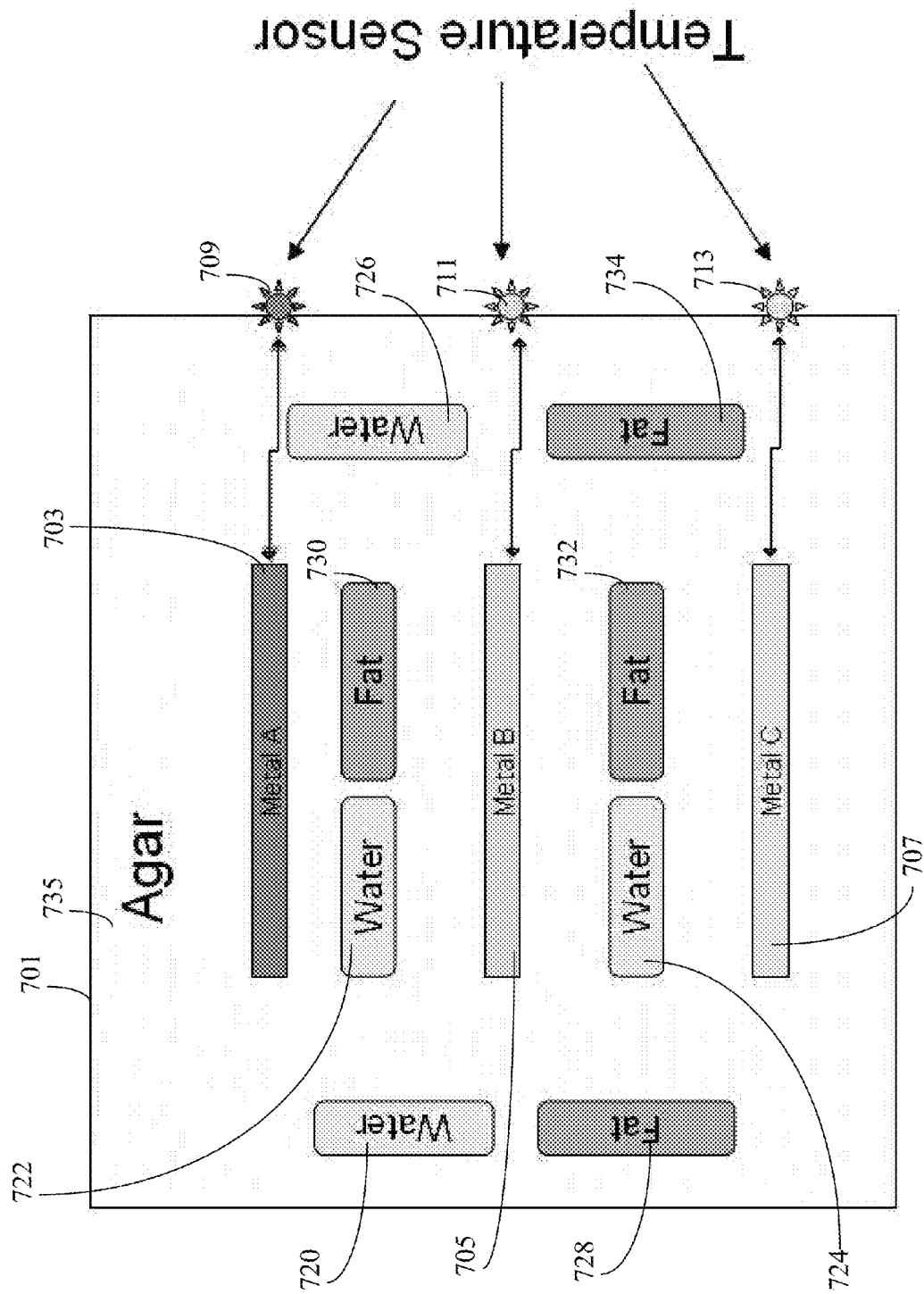
FIG. 7 shows a test object including different metal components, attached temperature sensors and adjacent water and fat components having regular shapes for use in MRI for evaluation of fat suppression methods, for example, according to invention principles.

FIG. 7 shows test object 701 including different metal components, attached temperature sensors and adjacent water and fat components having regular shapes for use in MRI for evaluation of fat suppression methods, for example. Metal components 703, 705, 707 are titanium, stainless steel and cobalt-chromium-molybdenum alloy, respectively, having attached temperature sensors 709, 711 and 713, respectively, with a resolution better than 0.1 C. Metal components 703, 705, 707 are regular in shape and of known dimensions, eg a rectangle of 10×10×50 mm. Multiple water components 720, 722, 724, 726 and fat mimicing components 728, 730, 732, 734 e.g. a tube with oils (mimicing fat) are placed adjacent to, and in the vicinity of, metal components 703, 705, 707 to evaluate MR fat suppression methods, like spectral fat saturation and DIXON methods, for example. In test object 701, the distance between metal components 703, 705, 707 is sufficient to avoid interference, i.e. overlay of signal voids or hyperintensity produced by one metal.

Figure 8:
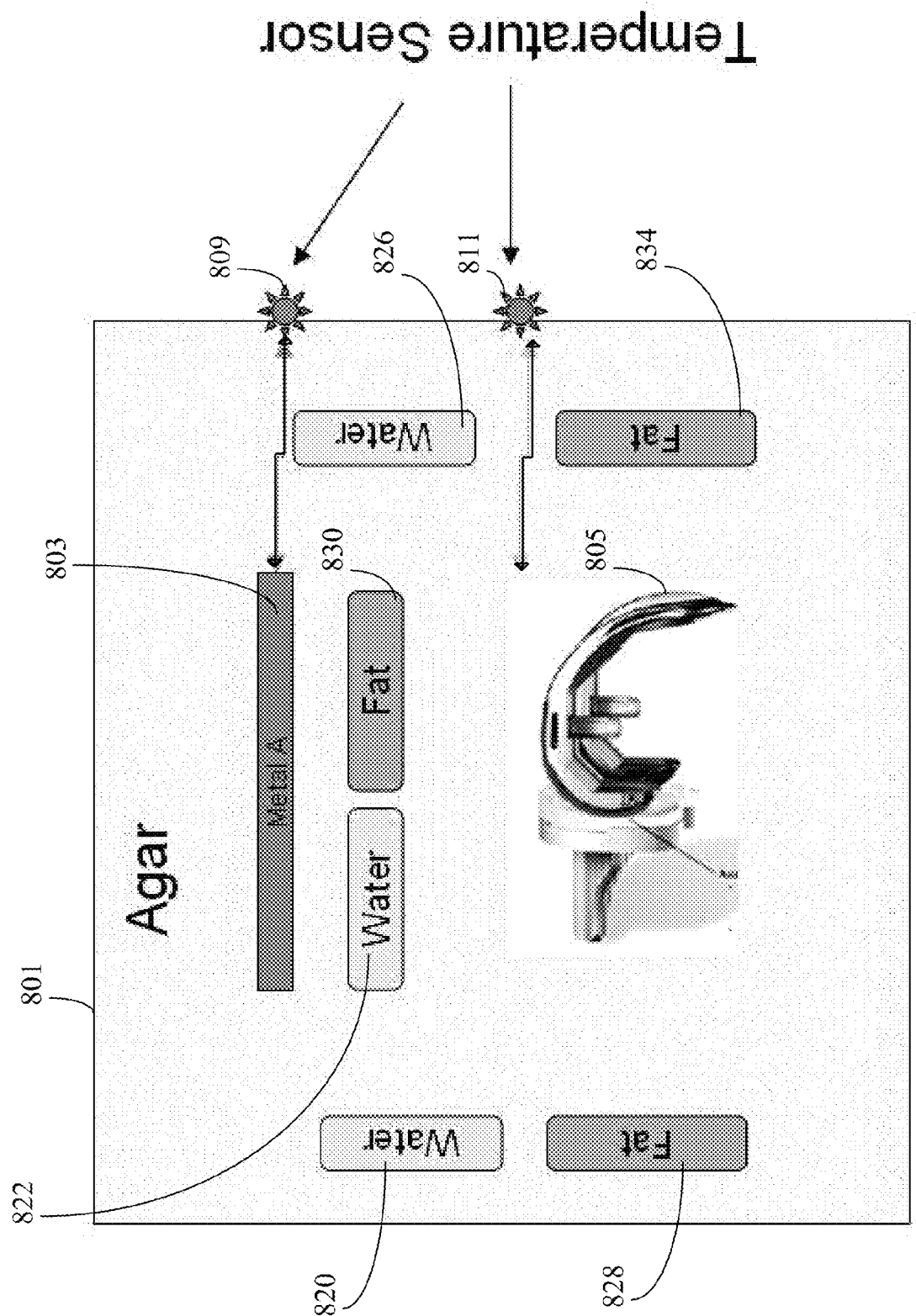
FIG. 8 shows a susceptibility test object including a regular shape metal component and a real metal implant of the same type of metal together with water and fat components around the metal parts and attached temperature sensors for use in fat suppression imaging evaluation, according to invention principles.

FIG. 8 shows susceptibility test object 801 including a regular shape metal component 803 and a real metal implant 805 made of the same type of metal together with water components 820, 822, 826 and fat components 828, 830, 834 around the metal parts, for use in MRI fat suppression imaging evaluation. Metal components 803, 805 are coupled to temperature sensors 809 and 811 having a resolution better than 0.1 C. Sensors 809, 811 are used to measure temperature changes of components 803, 805 which might be different due to different size of surfaces even though the same metal material is used by both components 803 and 805. Metal component 803 has a regular shape (rectangular, cylinder, tube or ball, for example) of known dimensions in order to calibrate and measure magnetic field susceptibility image artifacts. Water components 820, 822, 826 and fat mimicing components 828, 830, 834 e.g. a tube with oils (mimicing fat) are arranged in a similar fashion to test object 701. The advantage of this embodiment in comparison with previous one is Test object 801 provides accurate temperature measurement and magnetic field susceptibility related error (artifact) measurement.

Figure 9B:
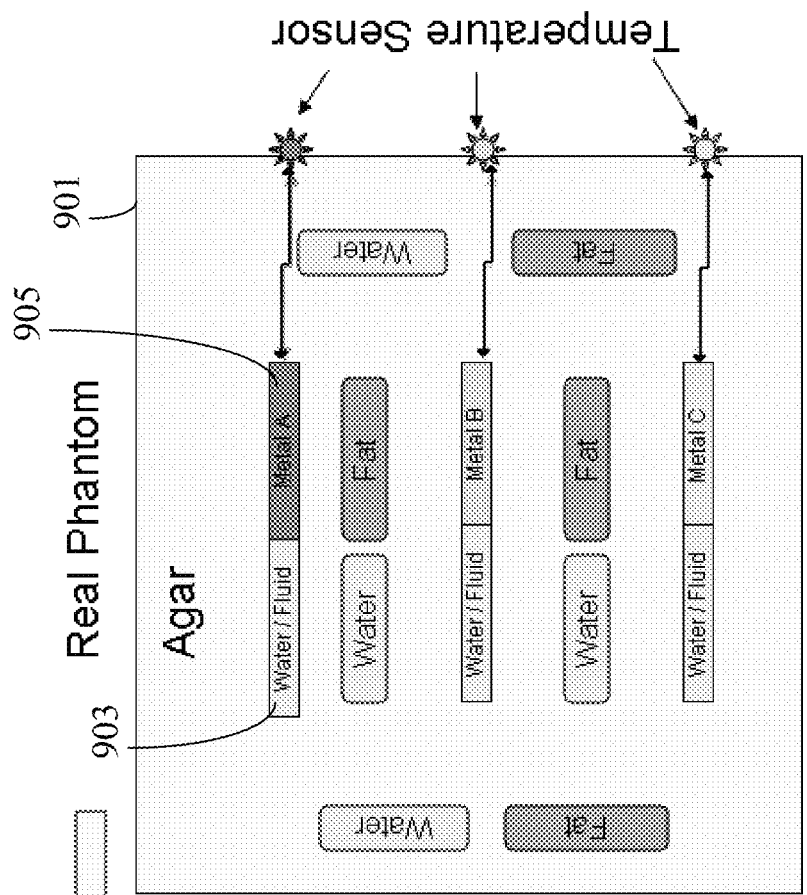
FIG. 9B shows a susceptibility test object including a regular shape metal component and an adjacent water or fluid component of the same size as the metal component and FIG. 9A shows a corresponding MR image of the FIG. 9B test object, according to invention principles.
Figure 9A:
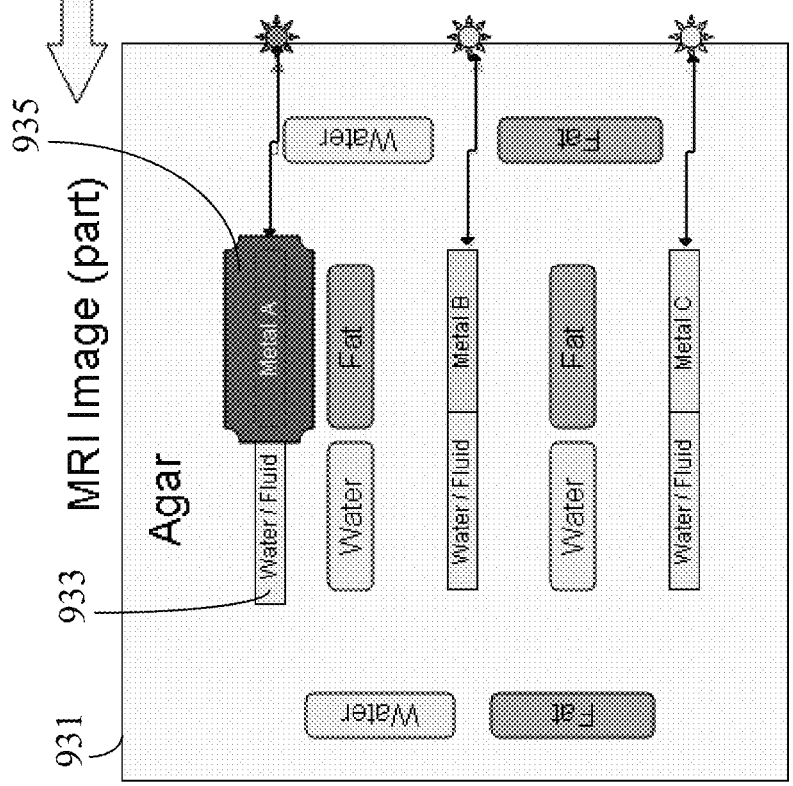

FIG. 9B shows a susceptibility test object 901 including a regular shape metal component 905 and an adjacent water or fluid component 903 of the same size as the metal component. FIG. 9A shows corresponding MR image 931 of test object 901. Water component image element 933 in image 931 of water component 903 is used to calibrate the size of metal component image element 935 of metal component 905 (either a regular size test component or a real metal implant), in order to evaluate effect of magnetic field susceptibility artifacts. Test object 901 enables system 10 to automatically calibrate and mark the real size of regular (or other) shape metal component 905 on image 931, which is not directly visible in MR image 931. Water or MR compatible fluid sample component 903 is adjacent to metal component 905. So in MRI image 931, the water component 933 is visible, and its width, for instance, is directly measured and one end is visible. Thereby, the size of metal component 935 can be calibrated based on size of component 933. In such a way, the susceptibility related artifacts, like distortion shown as signal voids, are quantitatively evaluated.

In a test object, metal, water and fat components may be adjacent or separated. The distance between different types of metals in one embodiment is at least 5 times the largest dimension of either object, i.e. if object diameter is 5 mm, the distance between metal objects is greater than 25 mm, for example. In one embodiment, the system adaptively iteratively images a test object with multiple different protocols to identify and automatically select an optimum imaging protocol for an implant of a particular metal type in response to measured distortion in a metal component image element compared with a water component of the same size and shape. In a further embodiment, the system adaptively selects an imaging protocol to use in imaging a particular test object in response to data indicating the metal type employed in the particular test object. Specifically, the system adaptively selects an MR imaging bandwidth (BW) parameter and slice encoding in response to data indicating the metal type employed in the particular test object.

System 10 (FIG. 3) adaptively selects an MR imaging bandwidth (BW) parameter for Titanium that is lower than for Cobalt. In one embodiment, the system adaptively selects an MR imaging bandwidth parameter for Cobalt that is substantially the highest available. The higher the BW, the lower the SNR (signal to noise ratio) and the longer the imaging time in order to obtain sufficient image quality. The system adaptively selects different slice encoding to reduce through plane artifacts (distortions). In one embodiment the system selects a slice encoding of 7 for Titanium, while for Cobalt, a slice encoding of 13 or greater is selected. The higher the slice encoding (number of slices per slab), the less artifacts but the longer the imaging time.

The system in one embodiment selects a specific image acquisition protocol for fat suppression in the presence of adjacent metal for a particular test object. Specifically, the system selects a Fat Suppression protocol from multiple different fat suppression MR imaging methods. The Fat Suppression MR imaging methods include, Spectral based fat suppression, STIR (Short Time Inversion Recovery) and a DIXON method. The Spectral based fat suppression method uses a pre-saturation pulse with fat resonance and water-excitation, requiring a substantially homogenous B0 field. However, due to strong susceptibility effect in presence of metal, this condition is significantly violated. STIR (Short Time Inversion Recovery) is substantially independent of B0 field but the B1 field may be altered in some degree due to metal presence. The main drawback of this method is that it suppresses not only fat but also some fluid e.g. related to a lesion and is commonly used for metal imaging with fat suppression. Further, the DIXON method needs to involve more than 3 points.

Figure 10:
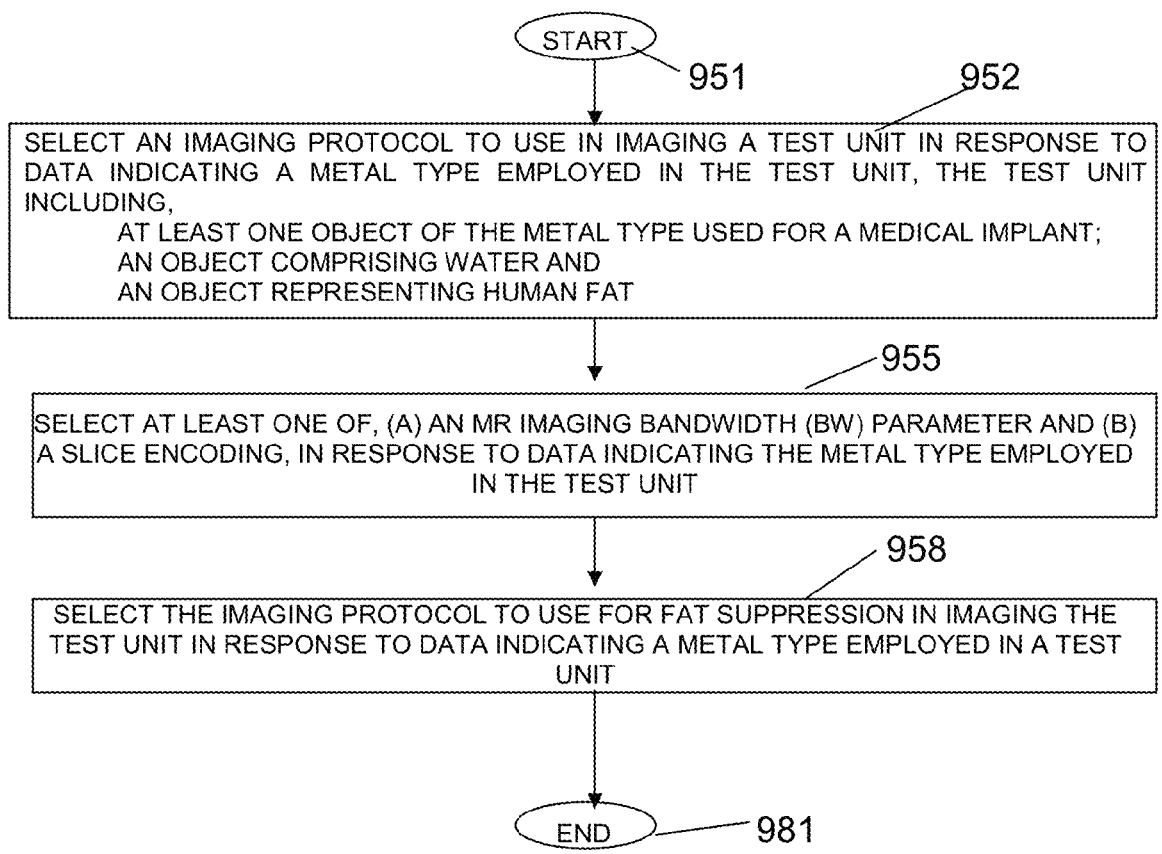
FIG. 10 shows a flowchart of a process used by a system for assessing quality of an image of human anatomical components in the presence of a metallic object, according to invention principles.

FIG. 10 shows a flowchart of a process used by system 10 (FIG. 3) for assessing quality of an image of human anatomical components in the presence of a metallic object. In step 952 following the start at step 951, image processor 15 selects an imaging protocol to use in imaging test unit 12 in response to data indicating a metal type employed in the test unit. Test unit 12 includes, at least one object of the metal type used for a medical implant; an object comprising water and an object representing human fat. The water object and fat object are less than 3 centimeters, for example, distant from the metal object. In step 955, image processor 15 selects at least one of, (a) an MR imaging bandwidth (BW) parameter and (b) a slice encoding, in response to data indicating the metal type employed in the test unit. In one embodiment, image processor 15 selects both an MR imaging bandwidth (BW) parameter and a slice encoding, substantially higher for cobalt than titanium. In step 958, image processor 15 selects the imaging protocol to use for fat suppression in imaging the test unit in response to data indicating a metal type employed in a test unit. Specifically, processor 15 selects an imaging protocol to use for fat suppression comprising one of, (a) a Spectral based fat suppression protocol using a pre-saturation pulse with fat resonance and water-excitation, (b) a STIR (Short Time Inversion Recovery) protocol and (c) a DIXON method imaging protocol. The process of FIG. 10 terminates at step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

DEFINITIONS

EPI comprises echo planar imaging involves image acquisition whereby a complete image is formed from a single data sample (k-space lines are acquired in one repetition time) of a gradient echo or spin echo sequence.

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted).

TI comprises inversion time, the time between an inversion recovery pulse and the next RF excitation pulse. TI determines the image luminance contrast.

$T_1$ comprises the longitudinal (or spin-lattice) relaxation time $T_1$ decay constant.

$T_2$ comprises the transverse (or spin-spin) relaxation time $T_2$ is the decay constant for a proton spin component.

TR comprises repetition time, the time between successive RF excitation pulses.

TE (Echo Time) comprises a time period between the start of an RF pulse and the maximum in the received echo signal. The sequence is repeated every TR seconds.

B0 is the main static base MRI magnetic field.

B1 is the RF transmit coil field.

Metallic Object is used herein to comprise an object with a substantial magnetic susceptibility effect that introduces prominent local B0 and B1 magnetic field changes and distortions and encompasses non-metallic and other such objects.

The system and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system provides specific test objects usable for gauging quality of MR metallic object images including soft tissue information for clinical diagnosis. Further, the processes and applications may, in alternative embodiments, be located on one or more (e.g., distributed) processing devices on a network linking the units of FIG. 1. Any of the functions and steps provided in FIGS. 1-10 may be implemented in hardware, software or a combination of both. No claim element herein is to be construed under the provisions of 35 U.S.C. 112, sixth paragraph, unless the element is expressly recited using the phrase "means for."

What is claimed is:

1. A test unit for imaging by an MR imaging system for use in assessing quality of an image of human anatomical components in the presence of a metallic object, comprising:
   at least one metal object of comprising a metal type used for a medical implant; an at least one water object comprising water; and
   an at least one fat object comprising a substance representing human fat,
   wherein at least one water object and at least one fat object are provided less than 3 centimeters distant from the at least one metal object; and wherein
   at least one of said at least one water object or said at least one fat object is of a known size and provided substantially adjacent to at least one of said at least one metal object; to facilitate a determination of an extent of degradation of an image quality based on a measurement of a size of said at least one water object or said at least one fat object of known size in an obtained image of said test unit.

2. A test unit according to claim 1, further comprising a temperature sensor coupled to said metal object.

3. A test unit according to claim 1, wherein:
   the at least one metal object comprises a plurality of metal objects; and
   each one of the plurality of metal objects is separated from a nearest one of the plurality of metal objects by a distance that is at least 5 times a minimum diameter of said metal objects.

4. A test unit according to claim 3, wherein
   at least two of said plurality of different metal objects are made of different metal types.

5. A test unit according to claim 4, wherein
   said different metal types include at least two of: (a) titanium, (b) stainless steel, (c) cobalt, and (d) a chromium-molybdenum alloy.

6. A test unit according to claim 1, wherein the test unit further comprises an agar material.

7. A test unit according to claim 1, wherein
   said at least one metal object comprises a real medical implant.

8. A test unit according to claim 1, wherein
   said water object is of known size and provided substantially adjacent to said metal object, and
   said water object is the same size as the metal object, to facilitate a determination of an extent of degradation of an image quality based on a measurement of a size of the water object of known size in an obtained image of said test unit.

9. A system for assessing quality of an image of human anatomical components in the presence of a metallic objects, comprising:
   an image processor configured to an imaging protocol to use in imaging a test unit in response to data indicating a metal type employed in said test unit, said test unit comprising:
   at least one metal object comprising said metal type, wherein said metal type is a metal that is used for a medical implant;
   at least one water object comprising water; and
   at least one fat object comprising a substance representing human fat,
   wherein the at least one water object and at least one fat object are each provided less than 3 centimeters distant from the at least one metal object; and wherein
   at least one of said at least one water object or said at least one fat object is of a known size and provided substantially adjacent to at least one of said at least one metal object; to facilitate a determination of an extent of degradation of an image quality based on a measurement of a size of said at least one water object or said at least one fat object of known size in an obtained image of said test unit.

10. A system according to claim 9, wherein
    said image processor selects at least one of: (a) an MR imaging bandwidth (BW) parameter, and (b) a slice encoding parameter, based on data indicating the metal type provided in said test unit.

11. A system according to claim 9, wherein
    said image processor selects both (a) an MR imaging bandwidth (BW) parameter and (b) a slice encoding parameter, based on data indicating the metal type provided in said test unit.

12. A system according to claim 9, wherein:
    said image processor selects both an MR imaging bandwidth (BW) parameter and a slice encoding parameter, and
    wherein each of said MR imaging bandwidth (BW) parameter and a slice encoding parameter is larger for said metal type being cobalt than for said metal type being titanium.

13. A system according to claim 9, wherein
    said image processor selects said imaging protocol to use for fat suppression in imaging said test unit in response to data indicating said metal type employed in said test unit.

14. A system according to claim 13, wherein
    said imaging protocol to use for fat suppression comprises at least one of: (a) a spectral-based fat suppression protocol using a pre-saturation pulse with fat resonance and water-excitation, (b) a STIR (Short Time Inversion Recovery) protocol, and (c) a DIXON method imaging protocol.

15. A method for assessing quality of an image of human anatomical components in the presence of a metallic object, comprising the activities of:
    selecting an imaging protocol to use in imaging a test unit in response to data indicating a metal type employed in said test unit, said test unit comprising:
    at least one metal object of comprising said metal type, wherein said metal type is a metal that is used for a medical implant;
    at least one water object comprising water; and
    an at least one fat object comprising a substance representing human fat,
    wherein at least one water object and at least one fat object being are provided less than 3 centimeters distant from the at least one metal object; and wherein
    at least one of said at least one water object or said at least one fat object is of a known size and provided substantially adjacent to at least one of said at least one metal object; to facilitate a determination of an extent of degradation of an image quality based on a measurement of a size of said at least one water object or said at least one fat object of known size in an obtained image of said test unit.

16. A method according to claim 15, further comprising the activity of:
    selecting at least one of: (a) an MR imaging bandwidth (BW) parameter, and (b) a slice encoding parameter, based on data indicating the metal type provided in said test unit.

17. A method according to claim 15, further comprising the activity of:
    selecting both (a) an MR imaging bandwidth (BW) parameter and (b) a slice encoding parameter, based on data indicating the metal type provided in said test unit.

18. A method according to claim 15, further comprising the activity of:
    selecting both an MR imaging bandwidth (BW) parameter and a slice encoding, parameter,
    wherein each of said MR imaging bandwidth (BW) parameter and said slice encoding parameter is larger for said metal type being cobalt than for said metal type being titanium.

19. A method according to claim 15, wherein said imaging protocol is an imaging protocol for fat suppression.

20. A method according to claim 19, wherein
    said imaging protocol comprises at least one of: (a) a spectral-based fat suppression protocol using a pre-saturation pulse with fat resonance and water-excitation, (b) a STIR (Short Time Inversion Recovery) protocol, and (c) a DIXON method imaging protocol.

* * * * *